United States Patent
Malik et al.

(10) Patent No.: US 8,395,773 B2
(45) Date of Patent: Mar. 12, 2013

(54) OPTICAL DEVICES AND METHODS FOR MEASURING SAMPLES

(75) Inventors: Imran R. Malik, Pasadena, CA (US); Axel Scherer, Laguna Beach, CA (US)

(73) Assignee: California Institute of Technology, Pasadena, CA (US)

( * ) Notice: Subject to any disclaimer, the term of this patent is extended or adjusted under 35 U.S.C. 154(b) by 290 days.

(21) Appl. No.: 12/820,104

(22) Filed: Jun. 21, 2010

(65) Prior Publication Data
US 2010/0321696 A1    Dec. 23, 2010

Related U.S. Application Data

(60) Provisional application No. 61/219,263, filed on Jun. 22, 2009.

(51) Int. Cl.
     *G01N 21/00*      (2006.01)
     *G01N 21/55*      (2006.01)
(52) U.S. Cl. .................... 356/432; 356/445; 356/318
(58) Field of Classification Search .......... 356/432, 356/440, 445–448, 300–301, 318
See application file for complete search history.

(56) References Cited

U.S. PATENT DOCUMENTS

| | | | | |
|---|---|---|---|---|
| 5,820,265 | A * | 10/1998 | Kleinerman | 374/137 |
| 6,222,619 | B1 * | 4/2001 | Herron et al. | 356/39 |
| 2002/0160534 | A1 * | 10/2002 | Herron et al. | 436/518 |
| 2004/0091862 | A1 | 5/2004 | Brandenburg et al. | |
| 2005/0024636 | A1 | 2/2005 | Nakamura | |
| 2006/0186346 | A1 | 8/2006 | Wei | |
| 2006/0289787 | A1 | 12/2006 | Ohmann et al. | |
| 2007/0084279 | A1 | 4/2007 | Huang et al. | 73/204.26 |
| 2010/0120164 | A1 * | 5/2010 | Salafsky | 436/164 |
| 2010/0152066 | A1 | 6/2010 | Malik et al. | |
| 2010/0321696 | A1 | 12/2010 | Malik et al. | 356/432 |
| 2011/0207137 | A1 * | 8/2011 | Malik et al. | 435/6.12 |

FOREIGN PATENT DOCUMENTS

| | | |
|---|---|---|
| JP | 2002-139418 | 5/2002 |
| WO | 2011/005487 | 1/2011 |

OTHER PUBLICATIONS

PCT International Search Report issued for PCT Application No. PCT/US2010/039389 filed on Jun. 21, 2010 in the name of California Institute of Technology et al.
PCT Written Opinion issued for PCT Application No. PCT/US2010/039389 filed on Jun. 21, 2010 in the name of California Institute of Technology et al.

* cited by examiner

*Primary Examiner* — Hoa Pham
(74) *Attorney, Agent, or Firm* — Steinfl & Bruno, LLP (57) ABSTRACT

Optical devices and methods for measuring samples while minimizing stray light are described. Such methods and devices are applicable to multiple fluid chambers with multiple sources as an integrated optical element. Light sources can be embedded onto a chip or microarray with multiple chambers, or can be part of an instrument arrangement.

25 Claims, 11 Drawing Sheets

OPTICAL DEVICES AND METHODS FOR MEASURING SAMPLES

CROSS REFERENCE TO RELATED APPLICATIONS

The present application claims priority to U.S. Provisional application No. 61/219,263, filed on Jun. 22, 2009 which is incorporated herein by reference in its entirety.

FIELD

The present disclosure relates to observing organic or inorganic samples. Moreover in particular, it relates to optical devices and methods for measuring samples.

BACKGROUND

Illumination of samples of various types is commonly practiced for many applications in medicine, biology, chemistry and other fields. Absorbance and fluorescence measurements are used in numerous applications. Dedicated instruments such as fluorescence microscopes tend to be bulky and expensive for portable applications as well as confocal optics due to various lenses, filters and opto-mechanical structures involved. The cost is high due to lenses, optical sources and various other elements involved in building a complete system.

In fluorescence related measurements, the problem of stray light can be significant. It can adversely affect the signal to noise ratio (SNR) and detection sensitivity. Typically, optical filters and dichroic mirrors are used which can be expensive. As the size of sample increases, the beam diameter increases, requiring larger optical elements and further increasing costs. Even a small sample of a few microliters can take up significant area if filled in a reservoir of small height.

SUMMARY

According to a first aspect, a method for detecting an illumination of a sample comprising: providing a sample to be illuminated, the sample being contained in an illumination chamber, providing a light source, providing a light guide positioned between the light source and the illumination chamber, providing an excitation filter positioned adjacent the light source in a propagation path of light rays from the light source, and providing a detector positioned over the illumination chamber, wherein: light rays from the light source propagate into one end of the light guide and exit another end of the light guide, said light rays entering the illumination chamber, said light rays illuminate said sample in the illumination chamber; and said detector captures illuminated light rays from said illuminated sample.

According to a second aspect, an optical system comprising: a light source and a light guide adjacent thereto, one or more illumination chambers, one or more illumination structures adjacent said light guide such that light from said light source propagate through said light guide to said one or more illumination chambers inside said one or more illumination structures, a lens over said one or more illumination chambers, and a detector over said lens and said one or more illumination chambers.

BRIEF DESCRIPTION OF DRAWINGS

These and other aspects will now be described in detail with the accompanying drawings, wherein.

DETAILED DESCRIPTION

In what follows, methods and arrangements utilizing a plurality of optics to obtain desired illumination while reducing a size of the system are described in accordance with various embodiments of the present disclosure.

Figure 1:
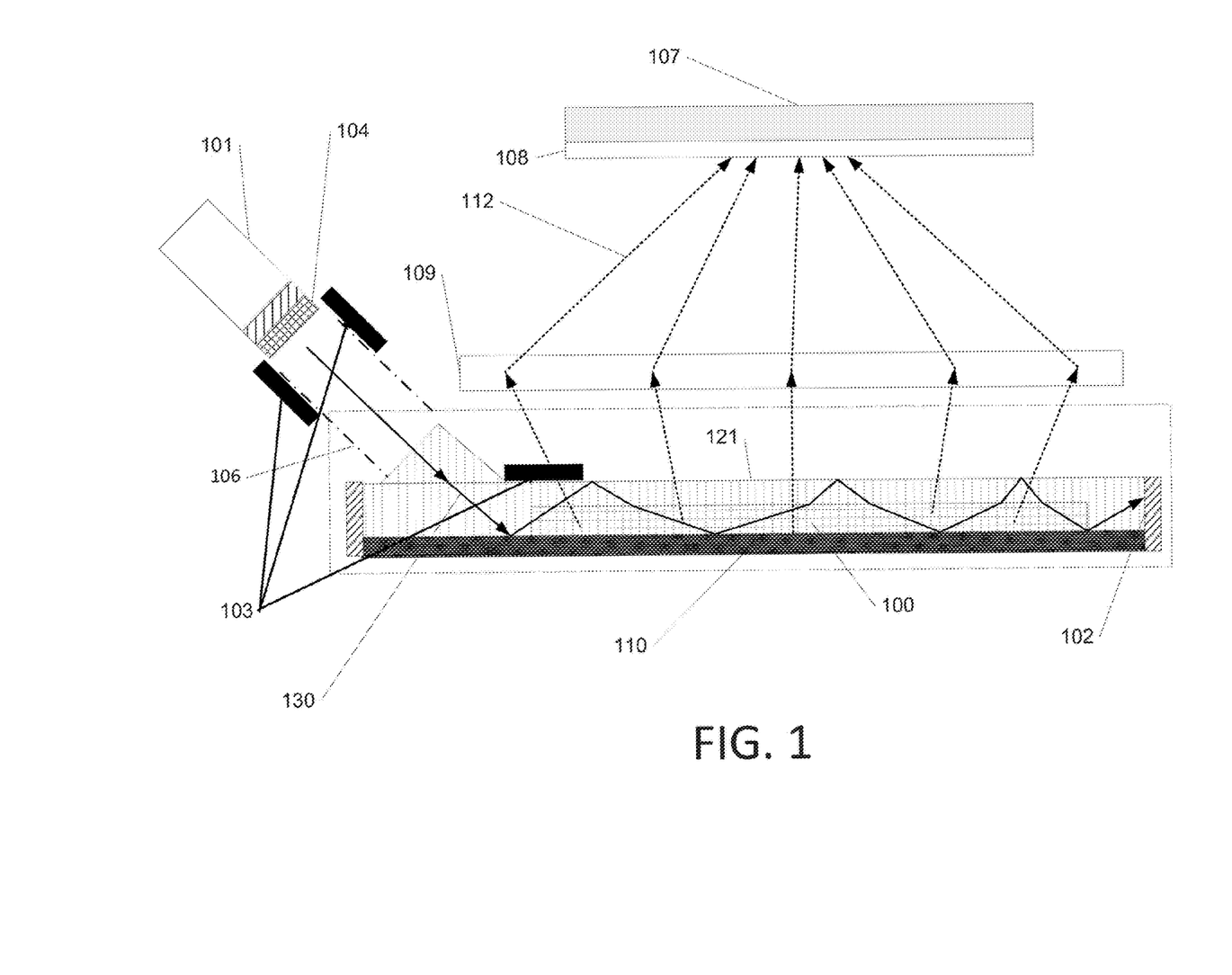
FIG. 1 shows a first embodiment of the disclosure.

FIG. 1 shows a schematic cross-sectional view of a combination of optical devices to obtain a desired illumination. The desired illumination may be, by way of example and not of limitation, absorbance or fluorescence observation of an illumination chamber (100) inside an illumination structure (121). A fluorescence observation involves providing an organic or inorganic sample, immersing with a chemical substance (e.g., fluorophore) and exposing the sample and the chemical substance to excitation light (130). The chemical substance absorbs energy from the excitation light, which comprises a particular wavelength and emits the excitation light as fluorescence rays (112). Absorbance observation involves comparing amplitudes of light rays entering a sample to the amplitude of the light rays leaving the sample to measure absorbance by the sample. The emitted fluorescence rays are captured and observed during desired applications of the described embodiment. For sake of simplicity, throughout the present disclosure, the term 'chamber' intends to indicate the illumination chamber and the term 'source' intends to indicate a light source.

In the embodiment of FIG. 1, a total internal reflection is utilized to guide an excitation light along a planar dimension of the chamber. A source (101) is positioned adjacent the chamber (100) and illumination structure (121) such that light rays from the source (101) propagate in a direction to eventually illuminate the chamber (100) and illumination structure (121). If desired, multiple sources can be positioned in varying geometries to further improve or optimize the illumination, and a divergence of the light rays from sources along a plane of the illumination structure (121) can be homogenized due to multiple reflections inside the light guide, thereby enabling uniformity in the illumination.

The source or sources can comprise, for example, common light emitting diodes (LEDs) (101). An excitation filter (104), may be optionally positioned adjacent the source (101) such that the light rays propagate through the excitation filter (104) before propagating toward the chamber (100) and illumination structure (121). The excitation filter (104) can select an excitation wavelength (105) from the source by filtering out undesired wavelengths. By way of example and not of limitation, LEDs designed for coupling into light guides (106) can also be provided such that the light rays from the source (101) propagate from the source (101), through the light guide (106), through the excitation filter (104) into the illumination structure (121) and the chamber (100) at a particular angle. The term 'light guide' is defined as an optical device that redirects and homogenizes propagating light rays in a desired direction. The light rays at an output of the light guide are more homogenous than at an input of the light guide, due to the multiple reflections. One or more reflectors (102) can be placed in various positions on an external surface of the illumination structure (121) (e.g., bottom surface (110) or side surfaces perpendicular to the bottom surface (102)) to cause the light rays to reflect inside the chamber. Additional layers of light sources can be stacked above the source (101), one upon another, to couple additional light where a height of the source (101) is smaller than a height of the chamber (100). Multiple light sources can also be stacked sideways, adjacent one another. The reflected excitation light propagates along a dimension parallel to the illumination structure (121), thereby illuminating the desired sample by multiple reflections and total internal reflection.

In the embodiment of FIG. 1, a detector (107) is positioned in a location over the chamber (100) to enable measuring of fluorescence rays. According to an embodiment, the detector (107) can be positioned over an optical structure (109) to collect light to capture the fluorescence rays in near field. The optical structure (109) can be an additional reflective light guide, optical lens element (e.g., polymer) or a combination of the additional reflective light guide and optical lens. The light guide (106) can have areas where the light is absorbed by way of light absorbing structures (103) to counter stray light (e.g., ambient light or undesired excitation light) from entering the light guide (106) or the detector (107). For example, in cases of fluorescence measurements, direct excitation light from the source (101) is not desired at the detector (107) (e.g., rather fluorescence rays emitted from the sample are desired at the detector). Light absorbing structures (103) reduce or eliminate excitation light from reaching the detector by allowing only certain angles from which the excitation rays can reach or enter the chamber (100). Light within a certain range of angles will stay inside the illumination structure (121) due to total internal reflection. A fluorescence filter can be positioned in a light path to further filter the light to obtain desired frequencies, prior to reaching the detector (107).

According to another embodiment, in case the size of the detector (107) is larger than a size of the chamber (100), the detector (107) can be positioned over the chamber (100) without providing further optical structures (109). Additional polymer lenses that can have a higher refractive index may be positioned over the chamber (100) to further couple the fluorescence rays from the chamber (100) to the detector (107). Furthermore, a second excitation wavelength filter (108) can be optionally positioned adjacent the detector (107) on the side of the fluorescence rays. The size of the detector (107) can be substantially smaller than the one or more polymer lenses (109) or reflectors (102), thereby lowering the cost of optical equipment.

According to another embodiment, the size of the detector (107) can be the same size as the chamber (100), thereby allowing more of the emitted fluorescence rays (112) to be directed to the detector than of those in a lens based optics device such as microscopes, due to numerical aperture issues. Increased light interactions, for example, due to multiple reflections, improve the chances of fluorophore becoming excited and emitting fluorescence rays. Furthermore, a large illumination structure (121) can comprise a larger sample region, thereby enabling increased light interaction between the light and the sample in the sample region. The improved illumination structure (121) can behave like a cavity to increase the interaction.

Further embodiments are shown in FIGS. 2-6, wherein alternative methods of coupling light from the source (101) are disclosed. In the methods of FIGS. 2-6, the excitation light from the chamber (100) is captured through a reflective light guide (120) which can also act as a stray light reducer such that light emitted from directions other than those emitted from the chamber (100) are blocked out by the reflective light guide (120). Inside portions of the reflective light guide (120) comprises reflective material and absorbing material to allow light emitted from the chamber (100) to reach the detector (107).

Figures 2, 3:
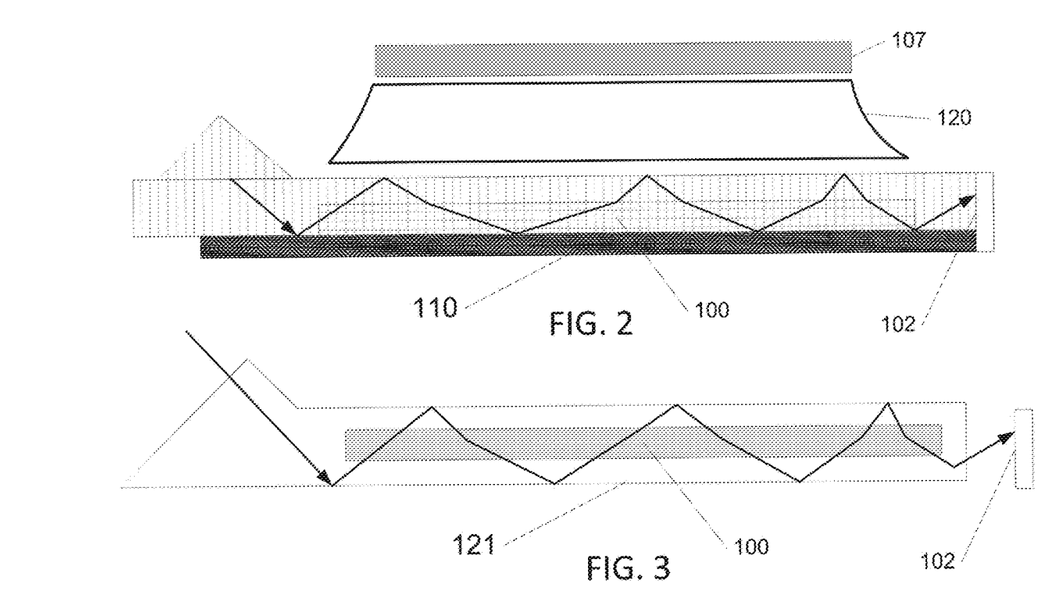
FIGS. 2-6 shows a cross-sectional view of various arrangements of a light guide.

According to an embodiment of FIG. 2, the bottom surface of the illumination structure (121) is reflective or metallic and a prism shaped structure, either a part of the illumination structure (121) or attached separately to an external structure couples light from the source to the illumination structure (121).

According to an embodiment of FIG. 3, the bottom surface of the illumination structure (121) lacks a reflective surface and depends on total internal reflection to illuminate the sample inside the chamber (100).

Figure 4:
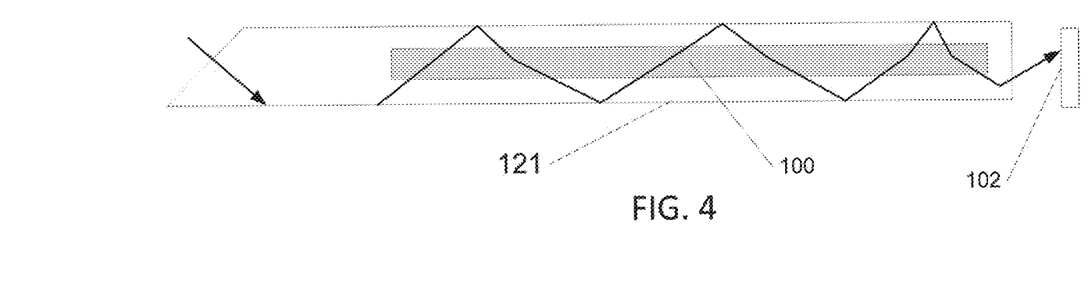

According to an embodiment of FIG. 4, a coupling structure smaller than the prism shaped structure is manufactured onto the illumination structure (121) which can result in ease of manufacturing. A laminate approach may be utilized to make such structures.

Figure 5:
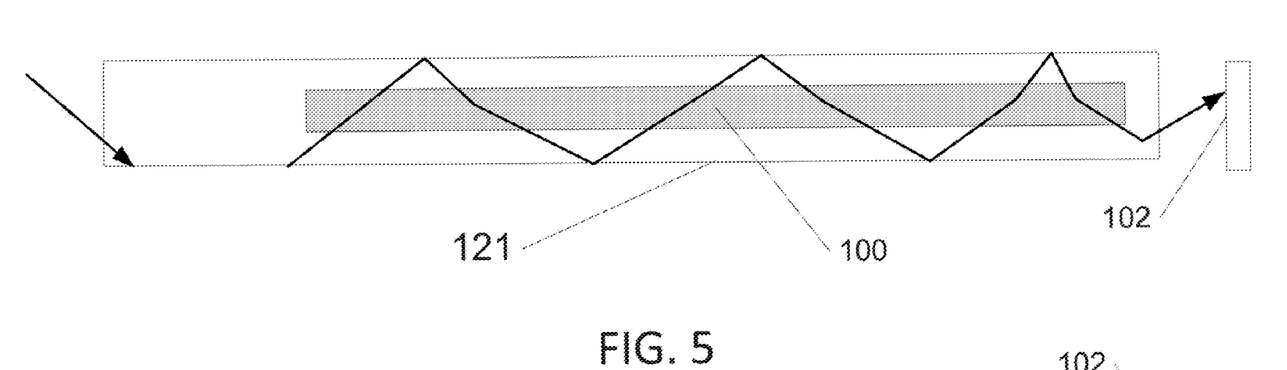

According to an embodiment of FIG. 5, the coupling structure is external to the illumination structure (121) and manufactured separately. Thus, the illuminations structure (121) and its support structure can be made by low cost methods, for example and not of limitation, xerography, lamination, or lithography. The coupling element can be, for example and not of limitation, prism shaped devices, lenses, light guides, or light guiding structures.

Figure 6:
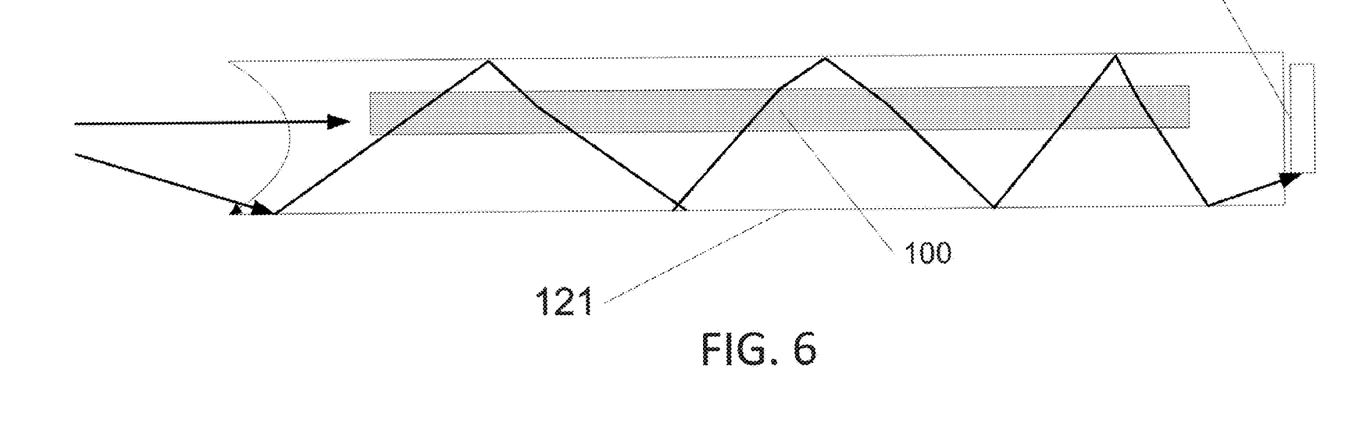

According to an embodiment of FIG. 6, a side of the illumination structure (121) is curved which can change angles of the incoming light to desired angles such that the light rays propagate inside the chamber (100).

Figure 7:
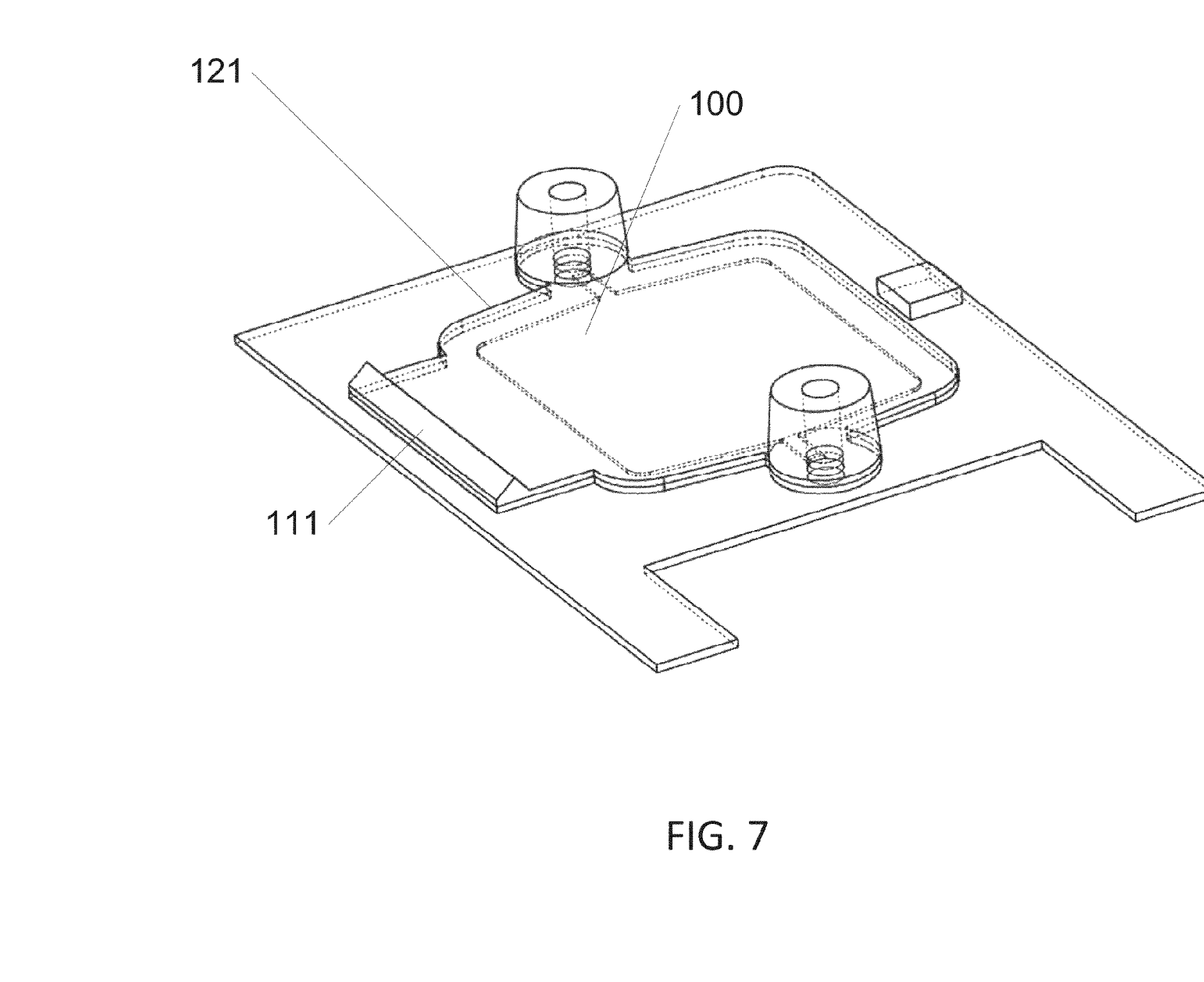
FIG. 7 shows three-dimensional view of a cartridge structure.

According to a further embodiment of FIG. 7, a cartridge structure is shown which can be used for fluorescence measurements, absorbance measurements or both simultaneously. Such a chamber can be used in applications for example and not limited to Real Time Polymerase Chain Reaction (PCR) or Enzyme-Linked Immunosorbent Assay (ELISA) hybridization studies.

Figure 8:
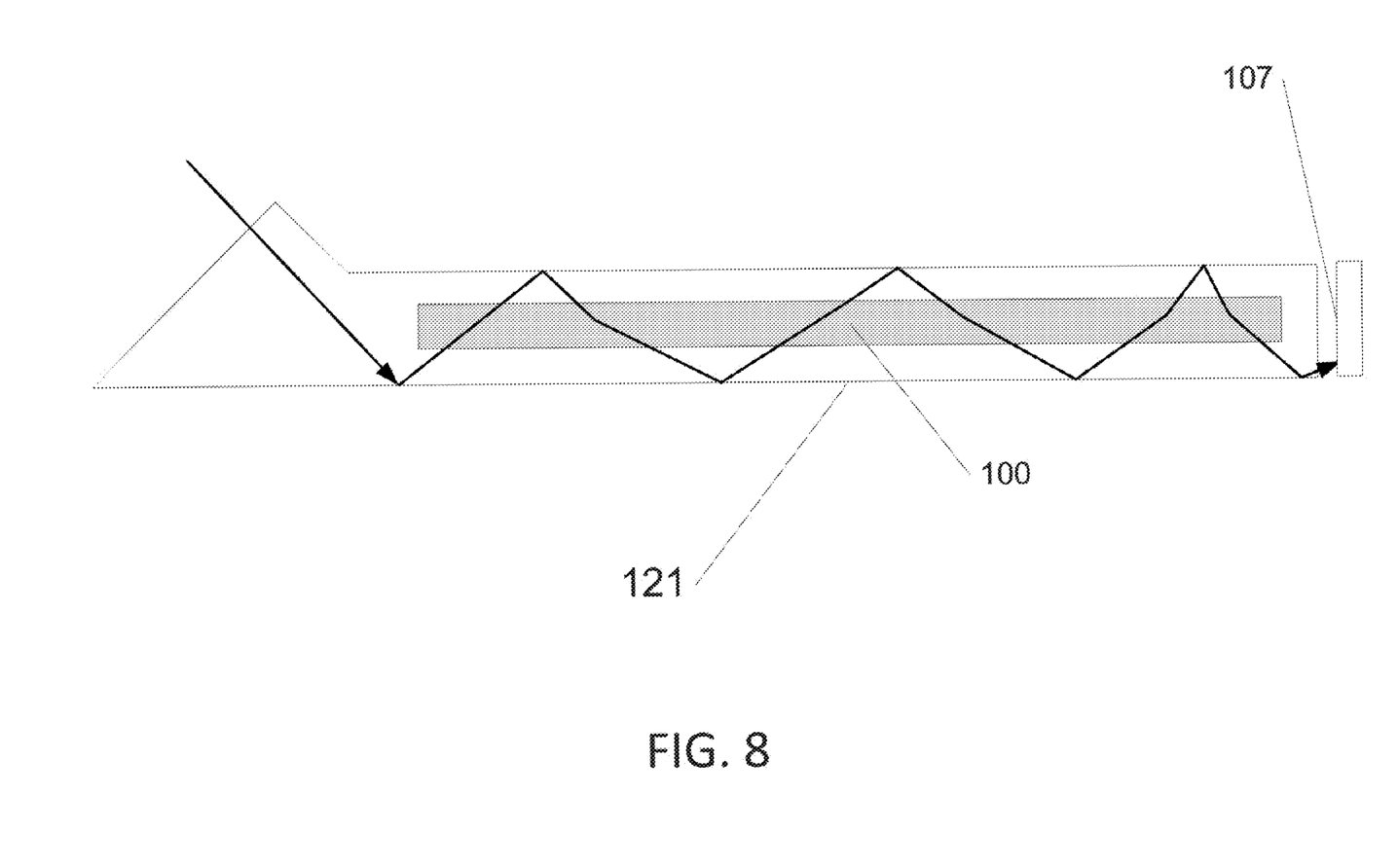
FIG. 8 shows a cross-sectional view of an absorbance measurement.

According to a further embodiment of FIG. 8, a schematic for absorbance measurement is shown, wherein the detector (107) is positioned in a lateral path of the propagating excitation light to increase the interaction distance of the light. The light reaching the detector (107) has reduced amplitude as a result of absorbance in the sample.

According to various embodiments of this disclosure, FIG. 1 shows a method of arranging optical devices to study properties of organic or inorganic substances of a single sample. An arrangement comprising common LEDs, filters and lenses enable low cost, portable and less bulky alternatives to conducting said studies as compared to methods found in prior art. A similar arrangement can be provided in a microarray or multiple chamber arrangement comprising integrated optical structures to enable simultaneously studying multiple samples with a single source and a single detector. Such arrangement comprises providing micro-lenses, micro-prisms and arrays of reaction wells.

Figure 9:
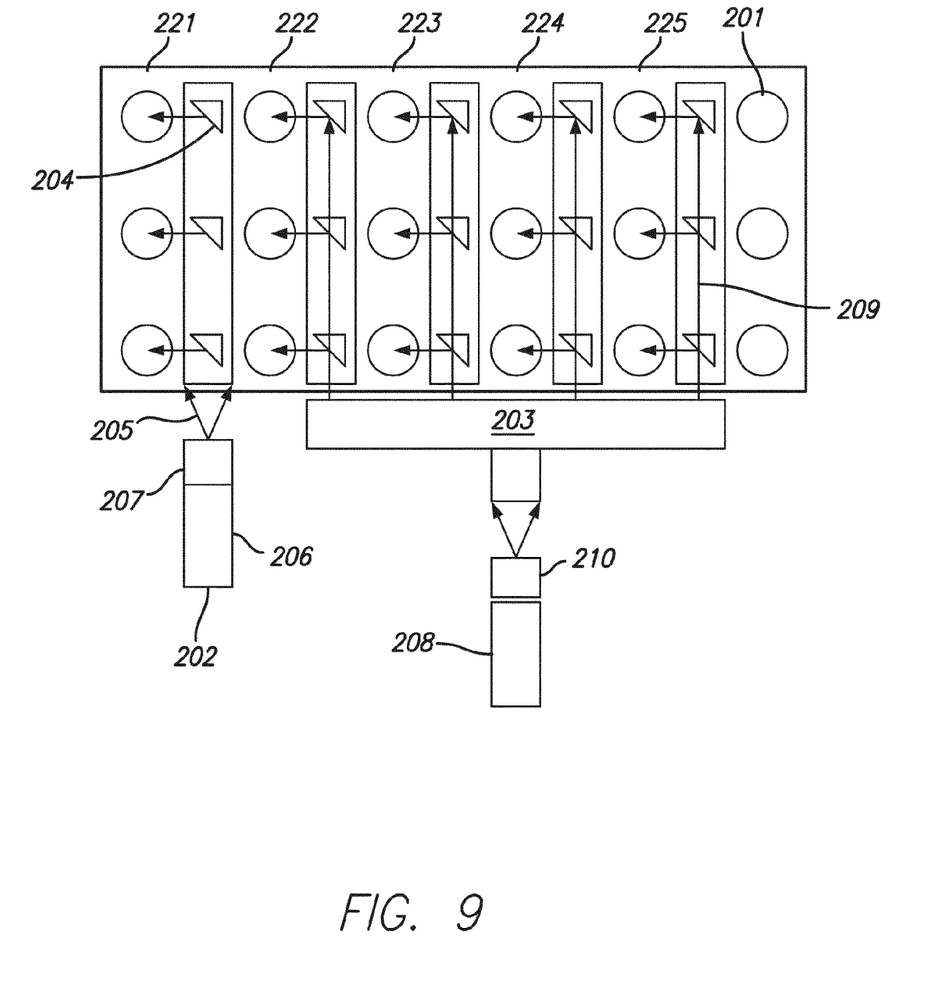
FIG. 9 shows a top-view of a microarray application of the embodiment of FIG. 1.

In accordance with a further embodiment of the disclosure, FIG. 9 shows a top-view of a similar method for measuring absorbance or fluorescence of multiple samples simultaneously. The optical system of FIG. 9 can be arranged in a microarray, which can be utilized in, for example, Real Time PCR or ELISA applications. Sources can be embedded onto a chip or microarray comprising multiple chambers, or reaction wells (201), or it can be provided externally. The embodiment of FIG. 9 comprises a plurality of reaction wells (201), arranged in an array, where the samples desired to be illuminated are placed and immersed with a reacting chemical such as fluorophore. In one example embodiment, as shown in a first column of the array (221), a single source (202) is positioned adjacent the column to be illuminated, wherein the source can be a common LED. Similar to the embodiment of FIG. 1, a light guide (206) is positioned adjacent the source (202) in a path of propagating light rays from the source (202) and an excitation filter (207) is positioned adjacent the light guide (206) to filter light rays exiting the light guide (206) such that only excitation light (205) of desired wavelengths propagate in a direction toward the reaction wells (201).

In an alternative embodiment of the disclosure from the first column (221) of FIG. 9, second through fifth columns (222-225) in FIG. 9 show a similar method for simultaneously measuring absorbance or fluorescence of multiple samples, where a single source (208) simultaneously illuminates more than one column (222-225). In case of fluorescence measurements, an excitation filter (210) is placed adjacent the source (208) and an integrated light guide (203) is positioned between the excitation filter (210) and the columns (222-225) to couple the light rays from the single source to the more than one columns (222-225) such that the light rays propagate in a direction of the reaction wells (201).

In accordance with a further embodiment, individual micro-lenses or micro-prisms (204) are positioned adjacent the reaction wells (201) to uniformly guide the propagating excitation light (209) to the array of individual reaction wells (201). Moreover, one side of the reaction wells (201) can be made reflective by means of a reflector to provide further illumination. The illumination from the reaction wells (201) can be imaged simultaneously using a two-dimensional detector (e.g., line scan detector), thereby eliminating the use of moving parts as realized in instruments such as fluorescence microscopes, thereby taking advantage of low cost small size optical elements such as filters.

In accordance with yet a further embodiment, the light guide (203) can be a part of an optical instrument provided with a source, such that the microarray comprising reaction wells (201) and micro-prisms or micro-lenses (204) can be aligned to the instrument for observation, further lowering the cost of the microchip.

In accordance with a further embodiment, the microarray can be injection molded or produced by a lithographic process comprising integrated optical elements, reaction wells (201), sources (202), and detectors.

Figure 10:
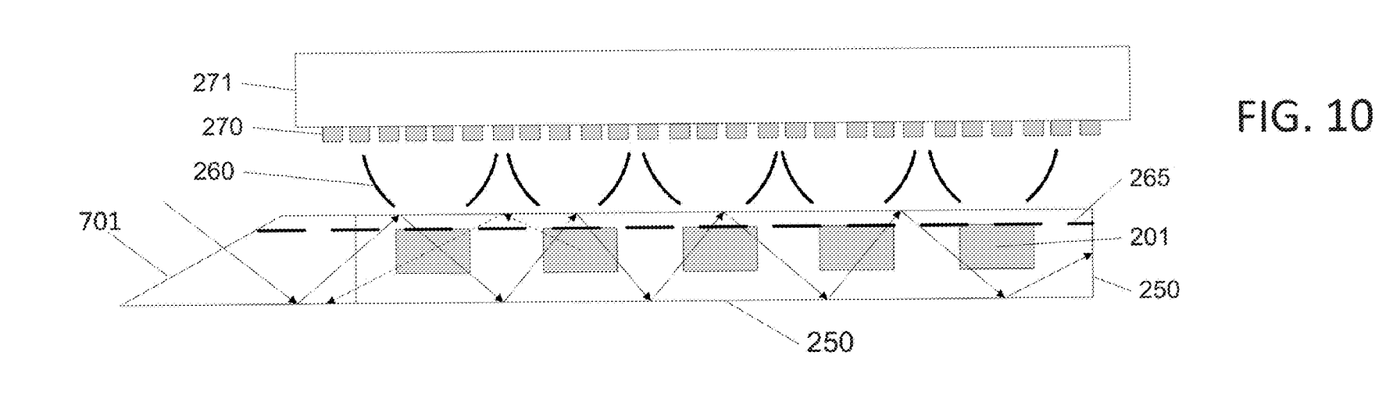
FIGS. 10-12 show cross-sectional views of microarray applications of the embodiment of FIG. 1.

According to a further embodiment of FIG. 10, a light guide structure (701) is utilized to collect light and reduce the cost of optics. The light guide can be attached to the structure, the detector (271) or separately. In case there are more pixels (270) on the detector than there are reaction wells (201), multiple pixels can collect light (260) for a particular reaction well. Multiple pixels can have different filters to allow multiplex measurements, where multiple frequency wavelengths are measured by a single detector. The array can be imaged from both top and bottom of the array to allow for multiplex measurements, which are particularly useful in PCR applications when air is used to change the temperature of the array. The illumination structure (121) can have an optional cover (265).

Figure 11:
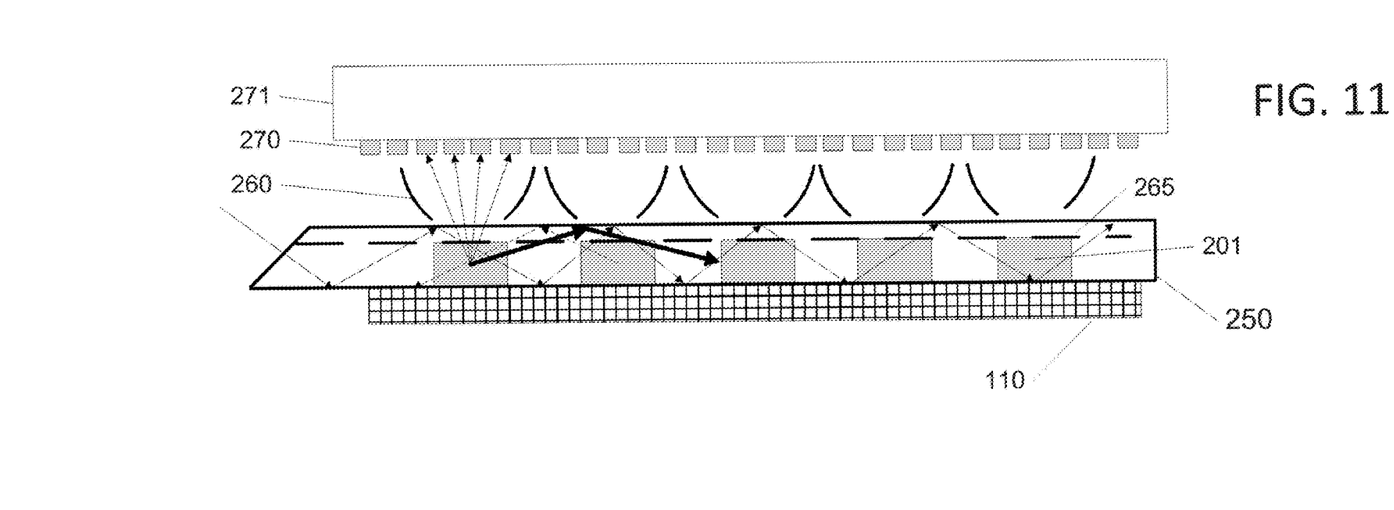

According to a further embodiment of FIG. 11, an arrangement is shown with a reflective bottom surface such that the array can be heated or cooled from bottom by contact heating and cooling as discussed in U.S. patent application Ser. No. 12/638,829, filed on Dec. 15, 2009, which is incorporated herein by reference in its entirety. This array can be used, for example and not of limitations, in ELISA measurements.

Figure 12:
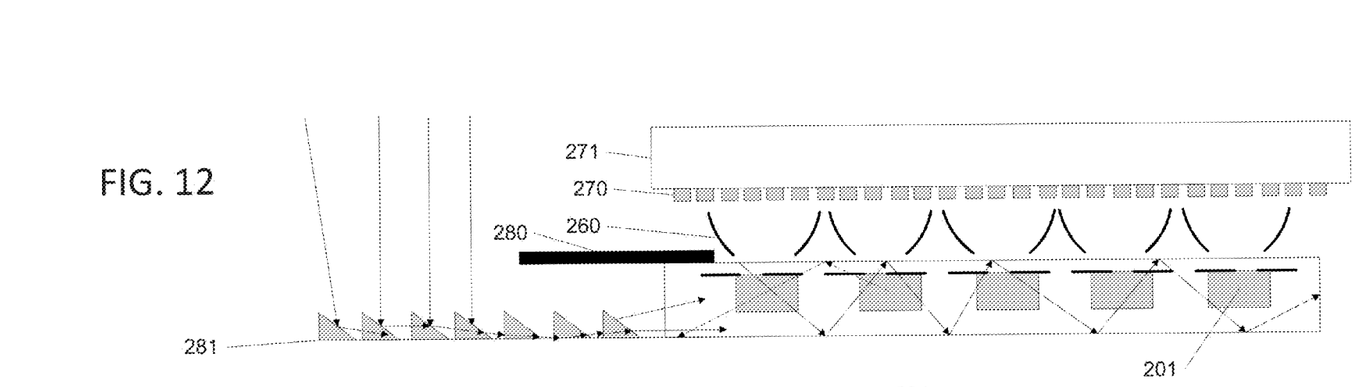

According to a further embodiment of FIG. 12, an alternate method of coupling light into the array or the single chamber of FIG. 1 is shown. A pattern of optical elements (281) (e.g., micro-prisms, micro-lenses, or micro-pyramids) are positioned adjacent the array or the chamber to direct excitation light in a desired direction. This method can allow high intensity light sources, and the light source can be positioned at or near perpendicular angles to the surface of the array. Additionally, the optical elements can be manufactured as part of the array (e.g., by injection molding). A film used for backlighting LCD panels and modules can be attached to the bottom surface of the array and a light absorbing element (280) can be positioned to absorb light at undesired angles from entering the array or reaching the detector.

Figure 13:
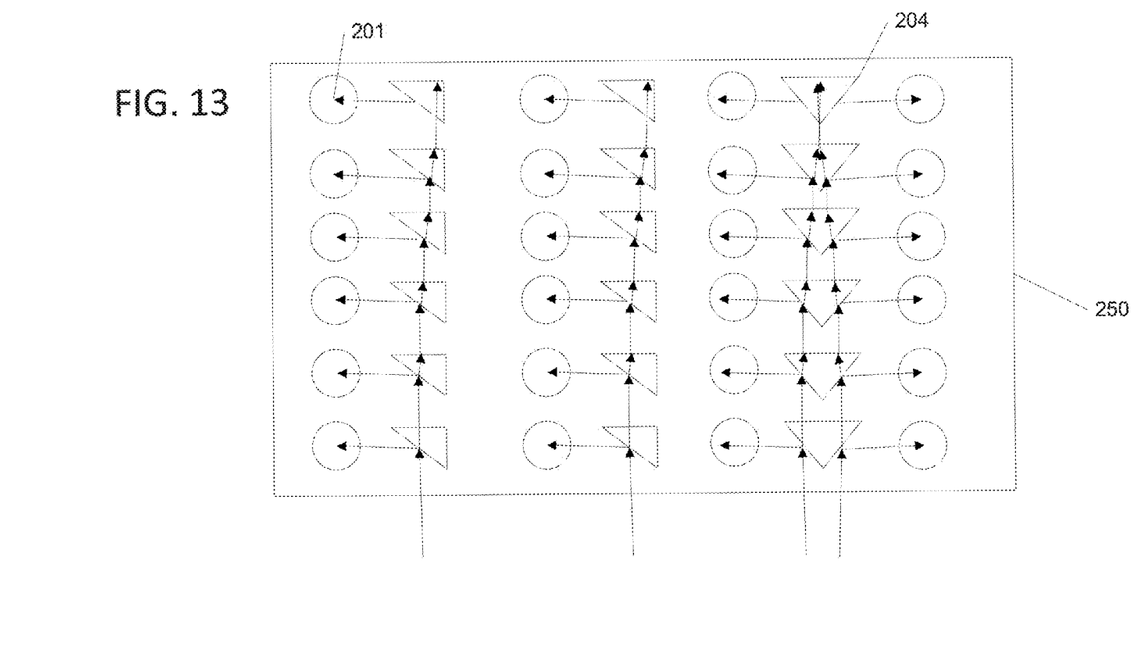
FIG. 13 shows a top-view of a microarray application of the embodiment of FIG. 1.

According to a further embodiment of FIG. 13, an alternate arrangement of optical elements are shown to illuminate the reaction wells of the array.

Figure 14:
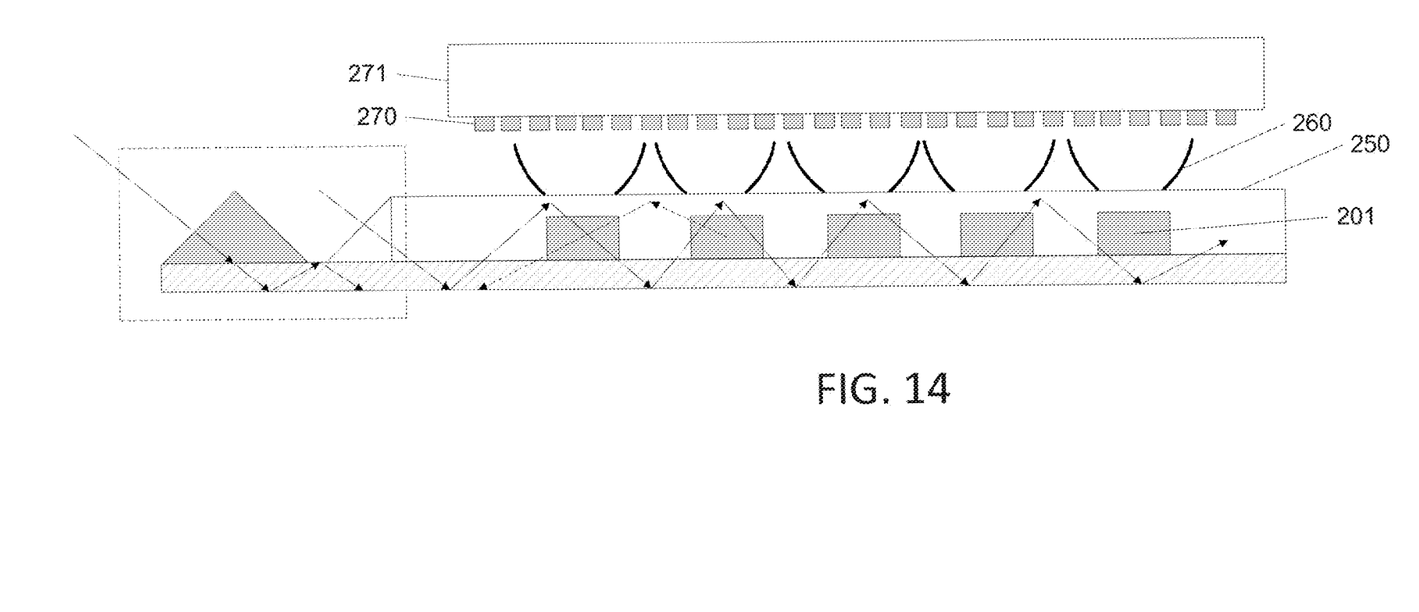
FIG. 14 shows a cross-sectional view of a microarray application of the embodiment of FIG. 1.

According to yet a further embodiment of FIG. 14, an external element is utilized as a coupling device where the external element can be a PDMS micro-fluidic chip, commercial microarray, or similar light coupling element.

Figure 15:
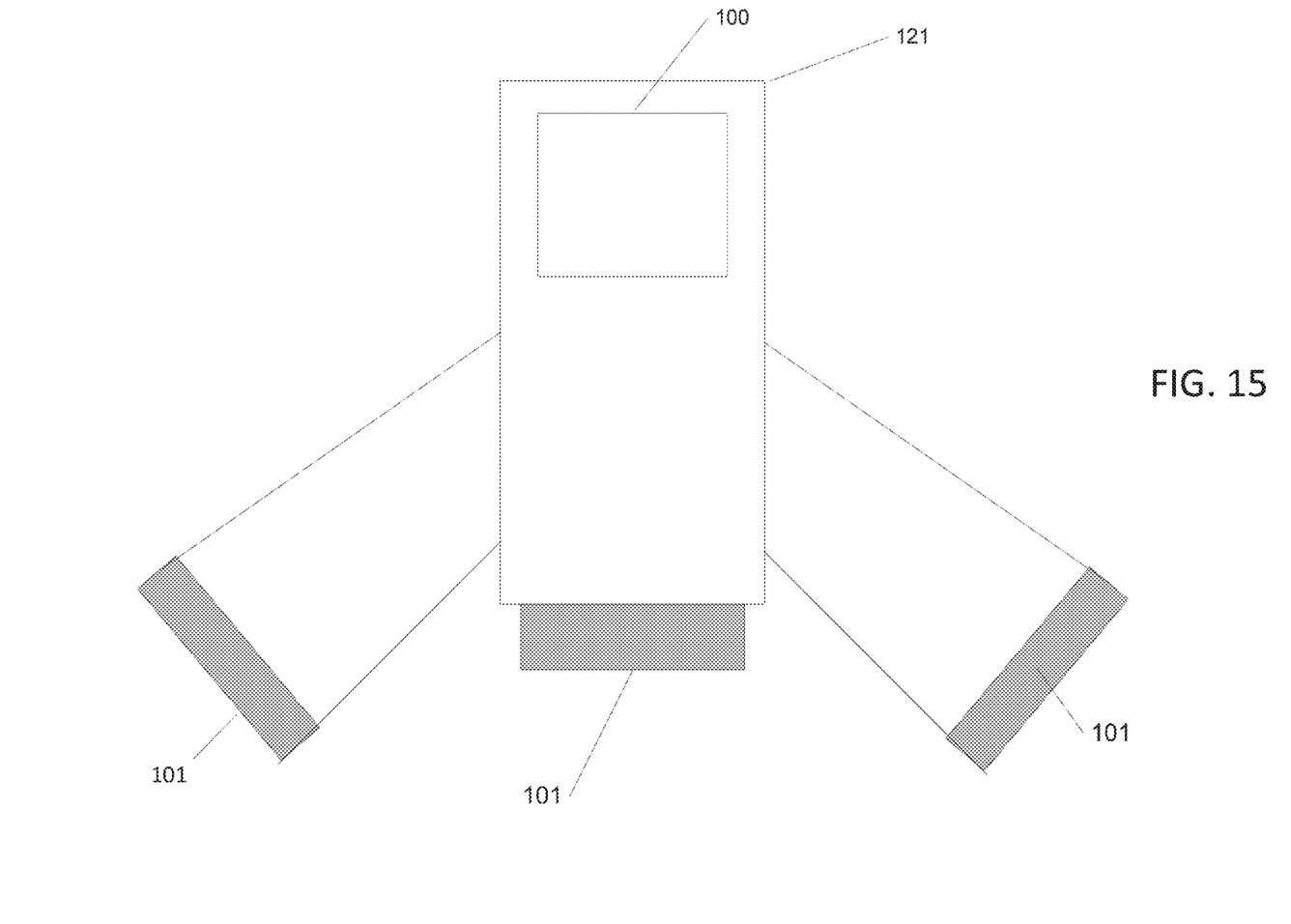
FIGS. 15-16 show top-views of a light guide with multiple light sources.
Figure 16:
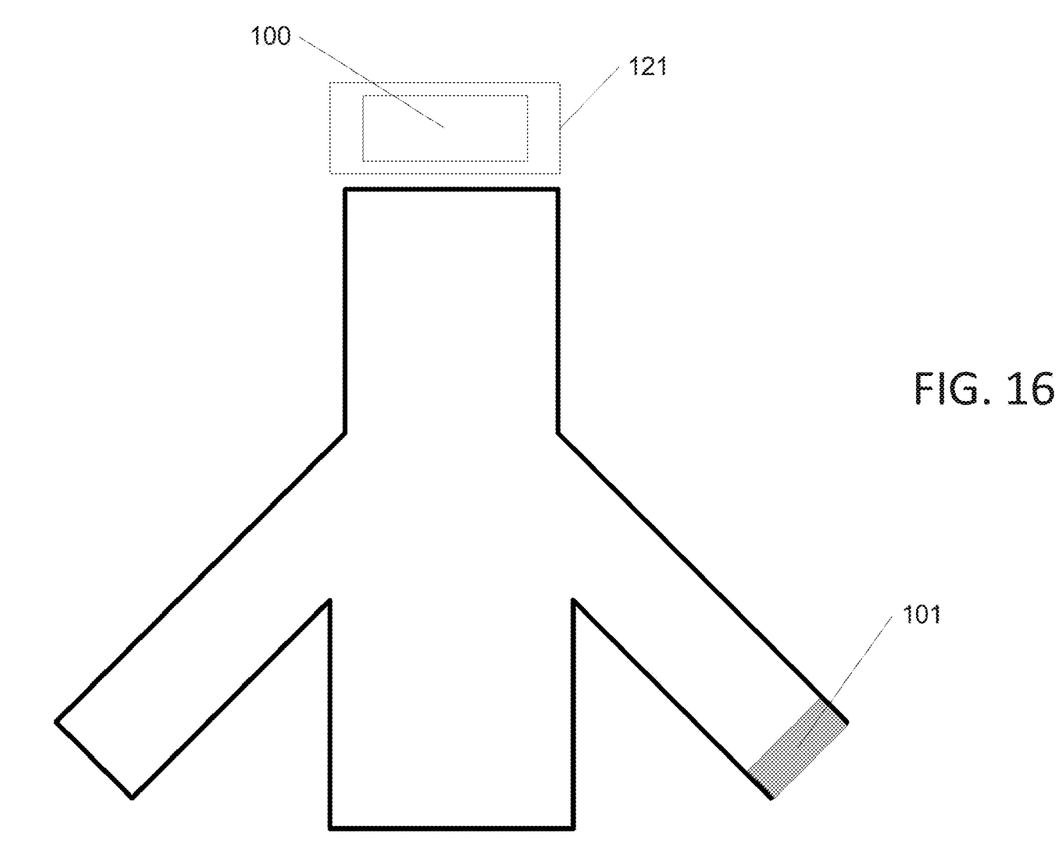

According to a further embodiment, FIGS. 15 and 16 show alternate optical arrangements when increasing the light source intensity is desired, multiple excitation wavelengths are desired, or further homogenization of light sources is desired. FIG. 15 shows a top-view of an arrangement, wherein the light guiding structure is a part of the illumination structure (121) assembly. FIG. 16 shows a top-view of an arrangement, wherein the light guiding structure is separate from the illumination structure (121) assembly. In both arrangements, up to three separate light sources (101) can be placed and the light is homogenized inside the light guide assembly. The combined, homogenized light at the output of the light guide assembly is of higher intensity than what would have been possible with a single light source. Different light sources can be used at each inlet, thus allowing for multiplex Real Time PCR applications.

When multiplex detection is desired, such that multiple frequencies are to be measured, various approaches can be applied. Multiple light sources with appropriate excitation filters can be arranged in an arrangement as in FIGS. 15 and 16. In an alternate embodiment, the detector can be divided up into regions, wherein pixels of different regions comprising different filters such that different regions of a single detector can accomplish the specified measurements. In another alternate embodiment, filters can be placed inside the light guide (or different pixels in case of array detectors) or in the path of the light propagation (e.g., by use of a sliding mechanism) such that different regions of the detector collect light that are filtered at different wavelengths.

For efficient use of light inside the illumination chamber, total internal reflection requires that light reflect between certain ranges of angles inside the chamber. For example, in a case where the illumination structure is made of COC and the chamber is filled with water, the range of angles which allows total internal reflection can be calculated by considering the refractive indices of the water and the COC.

The present disclosure has shown optical devices and methods for measuring samples. While configurations of optical apparatus have been described by means of specific embodiments and applications thereof, it is understood that numerous modifications and variation could be made thereto by those skilled in the art of optics without departing from the spirit and scope of the disclosure. It is therefore to be understood that within the scope of the claims, the disclosure may be practiced otherwise than as specifically described herein.

We claim:

1. A method for detecting an illumination of a sample comprising:
   providing a sample to be illuminated, the sample being contained in an illumination chamber;
   providing an illumination structure, the illumination chamber being contained in the illumination structure;
   providing a light source;
   providing a light guide positioned between the light source and the illumination structure;
   providing an excitation filter positioned adjacent the light source in a propagation path of light rays from the light source;
   providing a detector positioned over the illumination chamber, wherein:
   light rays from the light source propagate into one end of the light guide and exit another end of the light guide, said light rays entering the illumination structure;
   said light rays illuminate said sample in the illumination chamber;
   said detector captures illuminated light rays from said illuminated sample, the method further comprising:
   providing a light absorbing structure to remove undesired light, wherein said light absorbing structure comprises light guide light absorbing structures positioned adjacent to side walls of said light guide and an illumination chamber light absorbing structure positioned above a top surface of said illumination chamber.

2. The method of claim 1, further providing an emission filter, said emission filter placed in optical path between said illumination chamber and said detector.

3. The method of claim 1, further providing a coupling structure, said coupling structure placed between said light guide and said illumination structure to guide light into said illumination chamber.

4. The method of claim 1, wherein one or more reflective materials are positioned adjacent said illumination structure, said reflective material illuminating said illumination chamber by multiple reflections.

5. The method of claim 4, wherein said multiple reflections represent a total internal reflection.

6. The method of claim 1, further comprising the illumination structure with a bottom layer, said bottom layer comprising a reflective material.

7. The method of claim 1, wherein said light rays exiting the excitation filter are part of an excitation light at a specific wavelength.

8. The method of claim 1, further comprising one or more polymer lenses placed between the illumination chamber and the detector.

9. The method of claim 8, wherein the one or more polymer lenses are polydimethylsiloxane (PDMS) lenses.

10. The method of claim 1, further comprising providing a second excitation filter positioned adjacent the detector and between the detector and the illumination chamber.

11. An optical system comprising:
    a light source and a light guide adjacent thereto;
    one or more illumination chambers;
    one or more illumination structures adjacent said light guide such that light from said light source propagate through said light guide to said one or more illumination chambers inside said one or more illumination structures;
    a lens over said one or more illumination chambers;
    a detector over said lens and said one or more illumination chambers,
    wherein:
    said one or more illumination chambers are a plurality of one or more illumination chambers arranged in a microarray as reaction wells,
    said detector comprises a plurality of pixels, and
    when a number of the plurality of pixels is greater than a number of reaction wells, multiple pixels are adapted to be associated with a specific reaction well, different pixels of said multiple pixels being coupled with different filters, thus allowing measurement of multiple wavelengths in a single reaction well.

12. The system of claim 11, further comprising a reflective material located on a surface of said one or more illumination structures.

13. The system of claim 11, further comprising a light coupling structure, said light coupling placed between said light guide and said one or more illumination structures.

14. The system of claim 13, wherein said light coupling structure is manufactured as part of said one or more illumination structures.

15. The system of claim 13, wherein said light coupling structure is external and physically separate to said one or more illumination structures.

16. The system of claim 11, further comprising an excitation filter adjacent said light guide.

17. The system of claim 11, comprising a removing means to remove undesired light, placed over said light guide.

18. The system of claim 11, wherein said lens is a polydimethylsiloxane (PDMS) lens.

19. The system of claim 11, further comprising a second excitation filter positioned adjacent said detector, between said detector and said one or more illumination chamber.

20. The system of claim 11, wherein the light source provides illumination for a plurality of reaction wells in a single column of reaction wells.

21. The system of claim 11, wherein the light source provides illumination for more than one column of reaction wells.

22. The system of claim 21, wherein said light guide directs light rays from the light source to a plurality of columns of reaction wells.

23. The system of claim 11, further comprising micro-prisms or micro-lenses directing the light rays from the light source to individual reaction wells.

24. The system of claim 23, wherein said micro-prisms or micro-lenses are positioned adjacent the reaction wells or said microarray of reaction wells to direct the excitation light towards desired directions.

25. An optical system comprising:
    a light source and a light guide adjacent thereto;
    one or more illumination chambers;
    one or more illumination structures adjacent said light guide such that light from said light source propagate through said light guide to said one or more illumination chambers inside said one or more illumination structures;
    a lens over said one or more illumination chambers; and
    a detector over said lens and said one or more illumination chambers, wherein:
said one or more illumination chambers are a plurality of one or more illumination chambers arranged in a microarray as reaction wells, and
said light source and the light guide comprise a combination of:
a first light source and a first light guide, and
a second light source and a second light guide,
the first light source and the first light guide being adapted to provide illumination for a plurality of reaction wells in a single column of reaction wells and the second light source and the second light guide are adapted to simultaneously provide illumination for more than one column of reaction wells.

* * * * *